US009221738B2

(12) United States Patent
Broell et al.

(10) Patent No.: US 9,221,738 B2
(45) Date of Patent: Dec. 29, 2015

(54) METHOD AND SYSTEM FOR PURIFYING MONOMERS

(75) Inventors: Dirk Broell, Langen (DE); Christian Maul, Neustadt (DE); Benedikt Laux, Monzernheim (DE); Volker Schleep, Einhausen (DE)

(73) Assignee: Evonik Röhm GmbH, Darmstadt (DE)

( * ) Notice: Subject to any disclaimer, the term of this patent is extended or adjusted under 35 U.S.C. 154(b) by 707 days.

(21) Appl. No.: 13/256,469

(22) PCT Filed: Mar. 26, 2010

(86) PCT No.: PCT/EP2010/053963
§ 371 (c)(1),
(2), (4) Date: Sep. 14, 2011

(87) PCT Pub. No.: WO2010/127909
PCT Pub. Date: Nov. 11, 2010

(65) Prior Publication Data
US 2012/0000764 A1    Jan. 5, 2012

(30) Foreign Application Priority Data

May 6, 2009  (DE) .......................... 10 2009 002 861

(51) Int. Cl.
C07C 67/54       (2006.01)
C07C 51/573      (2006.01)
B01D 3/12        (2006.01)
B01D 3/42        (2006.01)

(52) U.S. Cl.
CPC ................ C07C 51/573 (2013.01); B01D 3/12 (2013.01); B01D 3/42 (2013.01); C07C 67/54 (2013.01)

(58) Field of Classification Search
CPC ....................................................... C07C 67/54
See application file for complete search history.

(56) References Cited

U.S. PATENT DOCUMENTS

| | | | |
|---|---|---|---|
| 2,463,608 A | | 3/1949 | Fein et al. |
| 3,816,267 A | * | 6/1974 | Chuang .............................. 203/8 |
| 4,983,761 A | | 1/1991 | Breuer et al. |
| 6,380,424 B1 | * | 4/2002 | Yoneda et al. ................. 560/209 |
| 6,548,696 B2 | * | 4/2003 | Kohlstruk et al. ............. 560/224 |

FOREIGN PATENT DOCUMENTS

| | | |
|---|---|---|
| CN | 1293185 A | 5/2001 |
| EP | 0 365 777 | 5/1990 |
| EP | 1 090 904 | 4/2001 |
| JP | 2-157246 A | 6/1990 |
| JP | 11-269159 A | 10/1999 |
| JP | 2002-138112 A | 5/2002 |
| JP | 2002-226436 A | 8/2002 |
| JP | 2008-297242 A | 12/2008 |

OTHER PUBLICATIONS

Office Action issued Feb. 17, 2014 in Japanese Patent Application No. 2012-508967 (submitting English translation only).
Maruzen K.K, "Kagaku Kogaku Binran", Chemical Engineering Handbook, 6$^{th}$ edition, Society for Chemical Engineers, Apr. 25, 2000, pp. 560-562 with English language translation.
Combined Chinese Office Action and Search Report issued Jul. 3, 2013, in Patent Application No. 201080016780.9 (with English-language translation).
Cvengros, J., et al., "Continuous Processes in Wiped Films. 2. Distilling Capacity and Separating Efficiency of a Molecular Evaporator with a Convex Evaporating Surface," Industrial & Engineering Chemistry Process Design and Development, vol. 17, No. 3, pp. 246-251, (1978) XP 002593163.
International Search Report issued Aug. 6, 2010 in PCT/EP10/053963 filed Mar. 26, 2010.
Combined Taiwanese Office Action and Search Report issued May 8, 2014 in Patent Application No. 099114045 (with English language translation).
Chinese Office Action issued Sep. 28, 2015 in Patent Application No. 201080016780.9 (with English Translation).
Modern Distillation Technology, Li Xingang being the chief editor, Chemical Industry Press, Mar. 2009, 1$^{st}$ Edition, 1$^{st}$ printing, Chapter 6, Molecular Distillation Technology and Application thereof, paragraph 1 on p. 170, pp. 174-179, 187 (with English Translation).
Book for Chemical Equipment Design—Vacuum Equipment Design, Fan Liqiu being the chief editor, Shanghai Science and Technology Press, Jan. 1990, 1$^{st}$ Edition, p. 118 (with English Translation).

* cited by examiner

*Primary Examiner* — Paul A Zucker
(74) *Attorney, Agent, or Firm* — Oblon, McClelland, Maier & Neustadt, L.L.P.

(57) ABSTRACT

The present invention relates to a process for purifying monomers, by evaporating at least a portion of the monomers present in a starting composition and then condensing it, which is characterized in that at least a portion of the starting composition is evaporated in a short-path evaporator, the mass flow density of the vapors $\dot{m}$ being selected according to the relation (I)

$$\dot{m} \leq 1800 \frac{\text{kg} \cdot \sqrt{K}}{\text{mbar} \cdot \text{m}^2 \cdot h \cdot \sqrt{\frac{\text{kg}}{\text{kmol}}}} \cdot p_i \cdot \left(\frac{\tilde{M}}{T}\right)^{0.5} \quad \text{(I)}$$

in which
$\tilde{M}$ is the average molar mass of the vapors in the short-path evaporator in kg/kmol
T is the temperature of the vapors in K
$p_i$ is the pressure in the short-path evaporator in mbar
$\dot{m}$ is the mass flow density of the vapors in kg/(m$^2$·h).
A further aspect of the present invention is a plant for performing the process.

18 Claims, No Drawings

METHOD AND SYSTEM FOR PURIFYING MONOMERS

The present invention relates to a process for purifying monomers. The present invention additionally describes a plant for performing this process.

Monomers are reactive compounds which can polymerize easily. Although this polymerization can be minimised in many cases by adding polymerization inhibitors, these compounds can lead to discoloration and side reactions. Moreover, relatively large amounts of stabiliser can adversely affect the further processing of the monomers in subsequent polymerization reactions, and so some specifications limit the content of stabilisers. The purification of monomers is therefore an ever-present problem. This is true especially for monomers with a high boiling point since they are purified under conditions under which polymerization can be suppressed only with relative difficulty, i.e. with high amounts of polymerization inhibitors. Accordingly, it is extremely difficult to obtain, in particular, very reactive monomers with a high boiling point in a very high purity without high yield losses. These monomers include, for example, hydroxyalkyl (meth)acrylates.

One preferred process for preparing and purifying hydroxyalkyl(meth)acrylates is described in European Patent Application EP-A-1 090 904. According to this, a reaction mixture which comprises hydroxyalkyl(meth)acrylates can be purified particularly efficiently by a distillation which is combined with a thin-film evaporator. The processes detailed in EP-A-1 090 904 lead to relatively pure products with high yields. However, particularly pure hydroxyalkyl(meth)acrylates are required for specific applications. For example, these monomers are used to produce contact lenses, as detailed, for example, in U.S. Pat. No. 4,375,534. The particularly high product purity needed for this purpose cannot be achieved with the process detailed in EP-A-1 090 904.

In view of the prior art, it was thus an object of the present invention to provide a process for purifying monomers, with which a particularly high purity is obtainable. At the same time, the product should as far as possible be obtained in high yields and, viewed overall, with low energy consumption. At the same time, it should be possible to minimise the concentration of stabiliser.

It was therefore a further object of the present invention to provide a process with which high-boiling monomers can be purified in a reliable and simple manner. In doing this, it should be possible especially to dispense with the use of large amounts of polymerization inhibitors. Furthermore, the monomers purified should have particularly small amounts of polymerization inhibitors, such that the inhibition of the monomer compositions can be matched to specific requirements which result from the further processing.

It was a further object of the present invention to provide a plant for performing the process. This plant should be inexpensive to construct and to operate. In particular, the plant should have long maintenance intervals and short shutdown times.

These objects, and further objects which are not stated explicitly but are immediately derivable or discernible from the connections discussed herein by way of introduction, are achieved by a process with all features of Claim 1. Appropriate modifications to the process according to the invention are protected in the dependent claims referring back to Claim 1. With regard to a plant for performing the process, Claim 18 provides a solution to the underlying problems.

The present invention accordingly provides a process for purifying monomers, by evaporating at least a portion of the monomers present in a starting composition and then condensing it, which is characterized in that at least a portion of the starting composition is evaporated in a short-path evaporator, the mass flow density of the vapours $\dot{m}$ being selected according to the relation (I)

$$\dot{m} \leq 1800 \frac{\text{kg} \cdot \sqrt{K}}{\text{mbar} \cdot \text{m}^2 \cdot h \cdot \sqrt{\frac{\text{kg}}{\text{kmol}}}} \cdot p_i \cdot \left(\frac{\tilde{M}}{T}\right)^{0.5} \quad (I)$$

in which
$\tilde{M}$ is the average molar mass of the vapours in the short-path evaporator in kg/kmol
T is the temperature of the vapours in K
$p_i$ is the pressure in the short-path evaporator in mbar
$\dot{m}$ is the mass flow density of the vapours in kg/(m²·h).

It is thus possible in an unforeseeable manner to provide a process for purifying monomers, with which a particularly high purity can be achieved. At the same time, the product can be obtained in high yields and, viewed overall, with low energy consumption.

By virtue of the process according to the invention, high-boiling monomers in particular can be purified in a reliable and simple manner. In doing this, it is especially possible to dispense with the use of large amounts of polymerization inhibitors. Furthermore, the monomers purified have particularly small amounts of polymerization inhibitors, such that the inhibition of the monomer compositions can be matched to specific requirements.

The present invention further provides a plant for performing the process. This plant can be constructed and operated inexpensively. In particular, the plant is notable for long maintenance intervals, short shutdown times and simple control.

According to the invention, at least a portion of a starting composition, comprising at least one monomer, is evaporated and then condensed. Of particular interest in this context are especially processes in which 5 to 95% by weight, more preferably 10 to 80% by weight and most preferably 20 to 60% by weight of the starting composition is evaporated. In continuous processes, this parameter is calculated from the proportion by weight of the purified monomer relative to the unevaporated proportions of the starting composition, which are discharged from the evaporator.

In this context, the term "starting composition" refers to the composition which is introduced into the short-path evaporator in order to evaporate and to condense the monomers.

Monomers in the present context are free-radically polymerizable compounds which have at least one carbon-carbon double bond which is preferably terminal.

These monomers include especially monomers with an acid group, monomers comprising ester groups and styrene monomers.

The acid group-containing monomers include, for example, monomers with a sulphonic acid group, for example vinylsulphonic acid; monomers with a phosphonic acid group, for example vinylphosphonic acid, and unsaturated carboxylic acids, for example methacrylic acid, acrylic acid, fumaric acid and maleic acid. Particular preference is given to methacrylic acid and acrylic acid.

The preferred monomers comprising ester groups include especially (meth)acrylates, fumarates, maleates and/or vinyl acetate. The expression "(meth)acrylates" encompasses methacrylates and acrylates, and also mixtures of the two. These monomers are widely known.

The monomers mentioned include (meth)acrylates which have 1 to 10 carbon atoms in the alkyl radical and have no double bonds or heteroatoms in the alkyl radical.

The (meth)acrylates which have 1 to 10 carbon atoms in the alkyl radical and have no double bonds or heteroatoms in the alkyl radical include (meth)acrylates with a linear or branched alkyl radical, for example methyl(meth)acrylate, ethyl(meth)acrylate, n-propyl(meth)acrylate, isopropyl(meth)acrylate, n-butyl(meth)acrylate, isobutyl(meth)acrylate, tert-butyl(meth)acrylate and pentyl(meth)acrylate, hexyl(meth)acrylate, 2-ethylhexyl(meth)acrylate, heptyl(meth)acrylate, octyl(meth)acrylate, 3-isopropylheptyl(meth)acrylate, nonyl(meth)acrylate, decyl(meth)acrylate; and cycloalkyl(meth)acrylates such as cyclopentyl(meth)acrylate, cyclohexyl(meth)acrylate, cyclohexyl(meth)acrylates with at least one substituent on the ring, such as tert-butylcyclohexyl(meth)acrylate and trimethylcyclohexyl(meth)acrylate, norbornyl(meth)acrylate, methylnorbornyl(meth)acrylate and dimethylnorbornyl(meth)acrylate, bornyl(meth)acrylate, 1-adamantyl(meth)acrylate, 2-adamantyl(meth)acrylate, menthyl(meth)acrylate and isobornyl(meth)acrylate.

A further class of monomers is that of (meth)acrylates with at least 11 carbon atoms in the alkyl radical, which derive from saturated alcohols and have no heteroatoms in the alkyl radical, for example undecyl(meth)acrylate, 5-methylundecyl(meth)acrylate, dodecyl(meth)acrylate, 2-methyldodecy(meth)acrylate, tridecyl(meth)acrylate, 5-methyltridecyl(meth)acrylate, tetradecyl(meth)acrylate, pentadecyl(meth)acrylate, hexadecyl(meth)acrylate, 2-methylhexadecyl(meth)acrylate, heptadecyl(meth)acrylate, 5-isopropylheptadecyl(meth)acrylate, 4-tert-butyloctadecyl(meth)acrylate, 5-ethyloctadecyl(meth)acrylate, 3-isopropyloctadecyl(meth)acrylate, octadecy(meth)acrylate, nonadecyl(meth)acrylate, eicosyl(meth)acrylate, cetyleicosy(meth)acrylate, stearyleicosyl(meth)acrylate, docosyl(meth)acrylate and/or eicosyltetratriacontyl(meth)acrylate; cycloalkyl(meth)acrylates such as 2,4,5-tri-t-butyl-3-vinylcyclohexyl(meth)acrylate, 2,3,4,5-tetra-t-butylcyclohexyl(meth)acrylate; heterocyclic(meth)acrylates such as 2-(1-imidazolyl)ethyl(meth)acrylate, 2-(4-morpholinyl)ethyl(meth)acrylate, 1-(2-methacryloyloxyethyl)-2-pyrrolidone, 2-(3-oxazolidinyl)ethyl methacrylate;
nitriles of (meth)acrylic acid and other nitrogen-containing methacrylates, such as N-(methacryloyloxyethyl)diisobutyl ketimine, N-(methacryloyloxyethyl)dihexadecyl ketimine, methacryloylamidoacetonitrile, N-3-dimethylaminopropyl(meth)acrylamide, 2-dimethylaminoethyl(meth)acrylate, 2-methacryloyloxyethylmethylcyanamide, cyanomethyl methacrylate;
aryl(meth)acrylates such as benzyl(meth)acrylate or phenyl(meth)acrylate, where the aryl radicals may each be unsubstituted or up to tetrasubstituted; (meth)acrylates with one hydroxyl group in the alkyl radical, especially 2-hydroxyethyl methacrylate (HEMA), 2-hydroxyethyl acrylate, hydroxypropyl methacrylate, especially 2-hydroxypropyl methacrylate and 3-hydroxypropyl methacrylate (HPMA), and/or hydroxypropyl acrylate, especially 2-hydroxypropyl acrylate and 3-hydroxypropyl acrylate, hydroxybutyl(meth)acrylate, preferably hydroxybutyl methacrylate (HBMA), 2,3-dihydroxypropyl(meth)acrylate, 3,4-dihydroxybutyl(meth)acrylate,
2,5-dimethyl-1,6-hexanediol(meth)acrylate,
1,10-decanediol(meth)acrylate,
glyceryl mono(meth)acrylate and
polyalkoxylated derivatives of (meth)acrylic acid, especially polypropylene glycol mono(meth)acrylate having 2 to 10, preferably 3 to 6, propylene oxide units, preferably polypropylene glycol monomethacrylate having approx. 5 propylene oxide units (PPM5), polyethylene glycol mono(meth)acrylate having 2 to 10, preferably 3 to 6, ethylene oxide units, preferably polyethylene glycol monomethacrylate having approx. 5 ethylene oxide units (PEM5), polybutylene glycol mono(meth)acrylate, polyethylene glycol polypropylene glycol mono(meth)acrylate;
(meth)acrylamides, especially N-methylol(meth)acrylamide, N,N-dimethylaminopropyl(meth)acrylamide, tert-butylaminoethyl methacrylate, methacrylamide and acrylamide;
glyceryl carbonate methacrylate;
2-carbamoyloxyethyl(meth)acrylate;
(2-oxo-1,3-dioxolan-4-yl)methyl(meth)acrylate,
(meth)acrylates which derive from unsaturated fatty acids or fatty acid amides, such as (meth)acryloyloxy-2-hydroxypropyl linolate, (meth)acryloyloxy-2-hydroxypropyl linolenate, (meth)acryloyloxy-2-hydroxypropyl oleate, heptadecenyloyloxy-2-ethyl(meth)acrylamide, heptadecadienyloyloxy-2-ethyl-(meth)acrylamide, heptadecatrienyloyloxy-2-ethyl(meth)acrylamide, heptadecenyloyloxy-2-ethyl(meth)acrylamide, (meth)acryloyloxy-2-ethyl-palmitoleamide, (meth)acryloyloxy-2-ethyloleamide, (meth)acryloyloxy-2-ethyl-eicosenamide, (meth)acryloyloxy-2-ethylcetoleamide, (meth)acryloyloxy-2-ethylerucamide, (meth)acryloyloxy-2-ethyllinoleamide, (meth)acryloyloxy-2-ethyllinolenamide, (meth)acryloyloxy-2-propylpalmitoleamide, (meth)acryloyloxy-2-propyloleamide, (meth)acryloyloxy-2-propyleicosenamide, (meth)acryloyloxy-2-propylcetoleamide, (meth)acryloyloxy-2-propylerucamide, (meth)acryloyloxy-2-propyllinoleamide and (meth)acryloyloxy-2-propyllinolenamide, and (meth)acrylates which derive from saturated fatty acids or fatty acid amides, such as (meth)acryloyloxy-2-hydroxypropyl palmitate, (meth)acryloyloxy-2-hydroxypropyl stearate and (meth)acryloyloxy-2-hydroxypropyl laurate, pentadecyloyloxy-2-ethyl(meth)acrylamide, heptadecyloyloxy-2-ethyl-(meth)acrylamide, (meth)acryloyloxy-2-ethyllauramide, (meth)acryloyloxy-2-ethylmyristamide, (meth)acryloyloxy-2-ethylpalmitamide, (meth)acryloyloxy-2-ethylstearamide, (meth)acryloyloxy-2-propyllauramide, (meth)acryloyloxy-2-propylmyristamide, (meth)acryloyloxy-2-propylpalmitamide and (meth)acryloyloxy-2-propylstearamide.

A further class of monomers is that of crosslinking monomers. These monomers have at least two double bonds with similar reactivity in a free-radical polymerization. These include especially (meth)acrylates with two double bonds, for example (meth)acrylates which derive from unsaturated alcohols, for example 2-propynyl(meth)acrylate, allyl(meth)acrylate, vinyl(meth)acrylate, and (meth)acrylates which derive from diols or higher polyhydric alcohols, for example glycol di(meth)acrylates such as ethylene glycol di(meth)acrylate, diethylene glycol di(meth)acrylate, triethylene glycol di(meth)acrylate, tetra- and polyethylene glycol di(meth)acrylate, 1,3-butanediol(meth)acrylate, 1,4-butanediol(meth)acrylate, 1,6-hexanediol di(meth)acrylate, glyceryl di(meth)acrylate, dimethacrylates of ethoxylated bisphenol A and diurethane dimethacrylate; (meth)acrylates with three or more double bonds, for example glyceryl tri(meth)acrylate, trimethylolpropane tri(meth)acrylate, pentaerythrityl tri(meth)acrylate, pentaerythrityl tetra(meth)acrylate and dipentaerythrityl penta(meth)acrylate.

The monomers additionally include vinyl esters such as vinyl acetate, vinyl chloride, vinyl versatate, ethylenevinyl acetate, ethylenevinyl chloride; maleic acid derivatives, for example maleic anhydride, esters of maleic acid, for example dimethyl maleate, methyl maleic anhydride; fumaric acid derivatives such as dimethyl fumarate; and (meth)acrylic anhydride.

A further group of monomers is that of styrene monomers, for example styrene, substituted styrenes with an alkyl substituent in the side chain, for example α-methylstyrene and α-ethylstyrene, substituted styrenes with an alkyl substituent on the ring, such as vinyltoluene and p-methylstyrene, halogenated styrenes, for example monochlorostyrenes, dichlorostyrenes, tribromostyrenes and tetrabromostyrenes.

Heterocyclic vinyl compounds such as 2-vinylpyridine, 3-vinylpyridine, 2-methyl-5-vinylpyridine, 3-ethyl-4-vinylpyridine, 2,3-dimethyl-5-vinylpyridine, vinylpyrimidine, vinylpiperidine, 9-vinylcarbazole, 3-vinylcarbazole, 4-vinylcarbazole, 1-vinylimidazole, 2-methyl-1-vinylimidazole, N-vinylpyrrolidone, 2-vinylpyrrolidone, N-vinylpyrrolidine, 3-vinylpyrrolidine, N-vinylcaprolactam, N-vinylbutyrolactam, vinyloxolan, vinylfuran, vinylthiophene, vinylthiolane, vinylthiazoles and hydrogenated vinylthiazoles, vinyloxazoles and hydrogenated vinyloxazoles;
maleimide, methylmaleimide;
vinyl and isoprenyl ethers; and
vinyl halides, for example vinyl chloride, vinyl fluoride, vinylidene chloride and vinylidene fluoride are further examples of monomers.

The present process can be used with surprising advantages especially to purify high-boiling monomers. High-boiling monomers are understood in the present context to mean monomers with a boiling point of at least 100° C., preferably at least 150° C. and more preferably at least 200° C. at standard pressure (1013 mbar).

Surprising advantages can be achieved especially in the case of purification of methacrylic anhydride or of methacrylates, especially of hexyl methacrylate, cyclohexyl methacrylate, 2-ethylhexyl methacrylate, 1,4-butanediol dimethacrylate, glycol dimethacrylate, 2-hydroxyethyl methacrylate, 2-ethoxyethyl methacrylate, decyl methacrylate, tetrahydrofurfuryl methacrylate, octadecyl/stearyl methacrylate, tetraethylene glycol dimethacrylate, 2,2-bis(hydroxymethyl)-1,3-propanediol dimethacrylate, 2-hydroxypropyl methacrylate, 3-hydroxypropyl methacrylate, 1,3-butanediol dimethacrylate, benzyl methacrylate, allyl methacrylate, 2-(2-butoxyethoxy)ethyl methacrylate, trimethylolpropane trimethacrylate, N-3-dimethylaminopropylmethacrylamide, 2-dimethylaminoethyl methacrylate, triethylene glycol dimethacrylate, isobornyl methacrylate, polyethylene glycol methacrylates, isodecyl methacrylate, dodecyl methacrylate, 2-[2-(2-ethoxyethoxy)ethoxy]ethyl methacrylate, 2,3-dihydroxypropyl methacrylate, (2-oxo-1,3-dioxolan-4-yl)methyl methacrylate, 2-carbamoyloxyethyl methacrylate and 1,6-hexanediol dimethacrylate, the purification of hydroxyalkyl methacrylates in particular being particularly preferred.

In a further aspect of the present invention, it is advantageously possible to use especially acrylic anhydride or acrylates. The acrylates, which can be purified in a surprisingly simple manner with the present process, include hexyl acrylate, cyclohexyl acrylate, 2-ethylhexyl acrylate, 1,4-butanediol diacrylate, glycol diacrylate, 2-hydroxyethyl acrylate, 2-ethoxyethyl acrylate, decyl acrylate, tetrahydrofurfuryl acrylate, octadecyl/stearyl acrylate, tetraethylene glycol diacrylate, 2,2-bis(hydroxymethyl)-1,3-propandiol diacrylate, 2-hydroxypropyl acrylate, 3-hydroxypropyl acrylate, 1,3-butanediol diacrylate, benzyl acrylate, allyl acrylate, 2-(2-butoxyethoxy)ethyl acrylate, trimethylolpropane triacrylate, N-3-dimethylaminopropylacrylamide, 2-dimethylaminoethyl acrylate, triethylene glycol diacrylate, isobornyl acrylate, polyethylene glycol acrylates, isodecyl acrylate, dodecyl acrylate, 2-[2-(2-ethoxyethoxy)ethoxy]ethyl acrylate, pentaerythrityl tetraacrylate, pentaerythrityl triacrylate and 1,6-hexanediol diacrylate.

The proportion of monomer to be purified in a starting composition for use in accordance with the invention is preferably at least 75% by weight, especially preferably at least 90% by weight, more preferably at least 95% by weight and most preferably at least 98% by weight. This proportion can be determined especially by gas chromatography.

In addition to customary product-related by-products, the starting composition may comprise polymerization inhibitors. The polymerization inhibitors for use with preference include especially phenol compounds, for example hydroquinones, hydroquinone ethers such as hydroquinone monomethyl ether, tert-butylhydroquinone, 2,6-di-tert-butylhydroquinone, 2,5-di-tert-butylhydroquinone, 2,4-dimethyl-6-tert-butylphenol or di-tert-butylpyrocatechol; p-phenylenediamines, for example N,N'-diphenyl-p-phenylenediamine, N,N'-di-2-naphthyl-p-phenylenediamine, N,N'-di-p-tolyl-p-phenylenediamine, N-1,3-dimethylbutyl-N'-phenyl-p-phenylenediamine and N-1,4-dimethylpentyl-N'-phenyl-p-phenylenediamine;
amines, for example thiodiphenylamine and phenothiazine;
copper dialkyldithiocarbamates, for example copper dimethyldithiocarbamates, copper diethyldithiocarbamates and copper dibutyldithiocarbamates;
nitroso compounds, for example nitrosodiphenylamine, isoamyl nitrite, N-nitrosocyclohexylhydroxylamine, N-nitroso-N-phenyl-N-hydroxylamine and salts thereof; and N-oxyl compounds, for example 2,2,4,4-tetramethylazetidine oxyl, 2,2-dimethyl-4,4-dipropylazetidine 1-oxyl, 2,2,5,5-tetramethylpyrrolidine 1-oxyl, 2,2,5,5-tetramethyl-3-oxopyrrolidine 1-oxyl, 2,2,6,6-tetramethylpiperidine 1-oxyl, 4-hydroxy-2,2,6,6-tetramethylpiperidine 1-oxyl, 6-aza-7,7-dimethyl-spiro[4,5]decane 6-oxyl, 2,2,6,6-tetramethyl-4-acetoxypiperidine 1-oxyl and 2,2,6,6-tetramethyl-4-benzoyloxypiperidine 1-oxyl; methylene blue, nigrosine base BA, 1,4-benzoquinone, sterically hindered phenols, for example 2,4-dimethyl-6-tert-butylphenol and/or tocopherol compounds, preferably α-tocopherol.

These compounds can be used individually or in the form of mixtures and are generally commercially available. For further details, reference is made to the standard technical literature, especially to Römpp-Lexikon Chemie; editors: J. Falbe, M. Regitz; Stuttgart, N.Y.; 10th edition (1996); under "Antioxidants", and the references cited here.

Surprising advantages can be achieved especially through the use of starting compositions which contain preferably 1 to 200 ppm, more preferably 5 to 150 ppm and most preferably 10 to 70 ppm of polymerization inhibitor.

Of particular interest in this context are especially starting compositions which comprise hydroquinone monomethyl ether, 4-hydroxy-2,2,6,6-tetramethylpiperidine N-oxyl, tocopherol, N,N-diethylhydroxylamine, ammonium N-nitrosophenylhydroxylamine (cupferron) and/or hydroquinone, without any intention that this should restrict the present invention. Surprising advantages are exhibited especially by starting compositions with a weight ratio of hydroquinone monomethyl ether to 4-hydroxy-2,2,6,6-tetramethylpiperidine N-oxyl in the range from 100:1 to 1:1, preferably in the range from 40:1 to 10:1.

In a further aspect of the present invention, preference is given to starting compositions which have at most a minor proportion of N,N'-diphenyl-p-phenylenediamine, N,N'-di-2-naphthyl-p-phenylenediamine, N,N'-di-p-tolyl-p-phenylenediamine, N-1,3-dimethylbutyl-N'-phenyl-p-phenylenediamine, N-1,4-dimethylpentyl-N'-phenyl-p-phenylenediamine, phenothiazine, nigrosine base BA and/or 1,4-benzoquinone, the proportion thereof being preferably at most 10 ppm, more preferably at most 1 ppm.

The process of the present invention is notable especially in that at least a portion of the starting composition is evaporated and condensed in a short-path evaporator. In a short-path evaporator, the condenser is arranged within the evaporator, such that the vapour pipe is dispensed with.

Surprising advantages can be achieved especially through the use of short-path evaporators in which the ratio of evaporator area to condenser area is in the range from 0.1 to 10.

In a particular configuration, it is possible to use a short-path evaporator which comprises a wiper system with which the starting composition to be evaporated is distributed homogeneously over the evaporator surface area. The preferred systems include roller wipers, flap wipers, pendulum flap wipers, rigid rotor wipers and scraping rotor wipers. In this context, surprising advantages can be achieved by the use of a scraping rotor, in which the wiper element is forced against the evaporator surface with spring tension.

According to the present invention, at least a portion of the starting composition is evaporated in a short-path evaporator. In this context, the relation (I) applies $$\dot{m} \leq 1800 \frac{\text{kg} \cdot \sqrt{K}}{\text{mbar} \cdot \text{m}^2 \cdot h \cdot \sqrt{\frac{\text{kg}}{\text{kmol}}}} \cdot p_i \cdot \left(\frac{\tilde{M}}{T}\right)^{0.5} \quad (I)$$

in which
$\tilde{M}$ is the average molar mass of the vapours in the short-path evaporator in kg/kmol
T is the temperature of the vapours in K
$p_i$ is the pressure in the short-path evaporator in mbar and
$\dot{m}$ is the mass flow density of the vapours in kg/(m²·h).

Accordingly, the conditions are selected such that the mass flow density of the vapours is less than or equal to the product of $$1800 \cdot p_i \cdot \left(\frac{\tilde{M}}{T}\right)^{0.5},$$

if the units are not shown for reasons of clarity. The mass flow density of the vapours is preferably less than or equal to the product of $$1700 \cdot p_i \cdot \left(\frac{\tilde{M}}{T}\right)^{0.5},$$

where the variables are each as defined above.

A high mass flow density of the vapours leads to a very economically viable process. In the case that the above-defined relation is exceeded, the purity and the quality of the product are adversely affected. In addition, a starting material with a high proportion of monomer surprisingly contributes to an unexpected improvement in quality.

The term "vapours" in the above relation refers to the gases which are evaporated in the evaporator and condensed in the condenser. Neglecting impurities, this term refers to the evaporated and condensed monomers.

The average molar mass of the vapours in the short-path evaporator is calculated from the molar mass of the components of the condensate. The average molar mass of the condensate can be determined by analysing the constituents of the condensate, which can be done, for example, by gas chromatography. In this context, the average relates to the number-average molecular weight.

The temperature of the vapours in relation (I) relates to the temperature between the evaporation area and the condensation area of the short-path evaporator. This temperature can be determined with a temperature sensor, especially a thermocouple or a resistance temperature sensor according to DIN IEC 60751 or DIN 43772. The temperature of the vapours or of the gas can be adjusted especially by means of the regulation of the pressure and of the number of particles in the evaporator.

The pressure relates to the pressure in the short-path evaporator and can be determined at the point at which the vacuum in the short-path evaporator is formed.

The pressure at which the evaporation is effected is in the range from $10^{-5}$ mbar to 10 mbar absolute, more preferably in the range from $10^{-4}$ mbar to 1 mbar absolute.

The mass flow density of the vapours $\dot{m}$ is calculated from the formula (II)

$$\dot{m} = \frac{\dot{M}}{A} \quad (II)$$

in which
$\dot{M}$ is the amount evaporated in kg/h and
A is the evaporator surface area in m².

The amount evaporated can be calculated via the amount of vapour condensate which is formed over a period of 1 hour. The evaporator surface relates here to the heated inner surface, by means of which the starting composition is evaporated in the short-path evaporator.

The upper limit of the mass flow density is calculated from the above relation (I). The lower limit is calculated especially from the efficiency of the process.

The mass flow density can be controlled especially via the evaporation energy supplied to the short-path evaporator, especially the temperature of the heating medium, and the amount of heat removed in the condensation of the vapour, especially the temperature of the coolant.

The evaporation is preferably performed at a temperature in the range from 15° C. to 150° C., more preferably in the range from 20 to 110° C. and most preferably 25° C. to 60° C., these figures being based on the mean temperature of the heating medium.

In a particular aspect, the condensation can be effected at a temperature in the range from −50° C. to 60° C., more preferably in the range from −25° C. to 50° C. and most preferably −7° C. to 35° C., these data being based on the mean temperature of the cooling medium.

The difference between the evaporation temperature and the condensation temperature may preferably be in the range from 1 to 180° C., more preferably 2 to 100° C. and most preferably 5 to 60° C.

The present purification process can preferably be performed continuously, in which case the mean residence time of the monomer may especially be in the range from 1 second to 5 minutes, more preferably in the range from 5 seconds to 3 minutes.

In the course of evaporation of the monomers to be purified, the starting composition comprises preferably at most 10% by weight, more preferably at most 5% by weight and most preferably at most 2% by weight of compounds having a boiling point which is at least 5° C. below the boiling point of the monomer to be purified. Accordingly, components with a low boiling point can be withdrawn from the starting composition before the monomers present in the starting composition are evaporated and condensed.

These components with a low boiling point can be removed from the starting composition especially by evaporation. The removal of the components with a low boiling point can preferably be performed in a short-path evaporator.

The pressure at which the components with a low boiling point are removed is preferably within a range from 1 mbar to 20 mbar, more preferably within a range from 2 mbar to 10 mbar. The temperature at which the components with a low boiling point are removed is preferably in the range from 40° C. to 150° C., more preferably in the range from 50° C. to 110° C., these figures being based on the mean temperature of the heating medium.

In a particular development, the residue obtained after the evaporation of at least a portion of the monomers from the starting composition can be worked up in order to remove monomer residues from this residue. This can be done especially by evaporating at least a portion of this residue in a short-path evaporator. The pressure at which the evaporation of a portion of the residue is effected is preferably within a range from $10^{-5}$ mbar to 10 mbar absolute, more preferably within a range from $10^{-4}$ mbar to 1 mbar. The evaporation of the residue can preferably be performed at a temperature in the range from 15° C. to 150° C., more preferably in the range from 20 to 110° C. and most preferably 25° C. to 60° C.

The monomers obtained from the residue are preferably purified once again by evaporation. To this end, the condensate obtained from the residue can be added to the starting composition, which can be done before or after the removal of components with a low boiling point.

The present process enables surprisingly high product qualities. For instance, the purified product may comprise at least 98% by weight, more preferably at least 99% by weight and most preferably 99.5% by weight of monomer.

In a particular aspect of the present invention, the monomers obtainable by the process may have a low colour number. For instance, the colour number after an inventive purification is at most 20, more preferably at most 10 and most preferably at most 5. The colour number can be determined especially by the process detailed in DE-A-10 131 479 (determination of the colour on the platinum-cobalt scale; also referred to as APHA or turbidity number), the process for determining the platinum-cobalt colour number detailed in the publication DE-A-10 131 479, filed at the German Patent and Trade Mark Office on Jun. 29, 2001 with the application number DE 101 31 479.5, being incorporated into this application for the purposes of disclosure. This process was developed on the basis of DIN EN ISO 6271.

Surprisingly, the present invention can provide a monomer composition whose colour number, even after storage at 30° C. over a period of 6 months, increases by at most 5 units.

A preferred plant for performing the process according to the invention may comprise at least three short-path evaporators, the short-path evaporators being connected to one another such that the residue from the first short-path evaporator is passed into the second short-path evaporator and the residue from the second short-path evaporator is passed into the third short-path evaporator.

This plant is novel and therefore likewise forms part of the subject-matter of the present invention.

In a further aspect of the present invention, the starting composition can be purified more than once, especially twice, three times, four times or more frequently, with a short-path evaporator, in which case at least a portion of the particular residue is evaporated and condensed once more.

In addition, embodiments of the present process which are of interest are also those in which the starting composition is purified more than once, especially twice, three times, four times or more frequently, with a short-path evaporator, in which case at least a portion of one or more condensates is evaporated and condensed once more.

The present invention will now be illustrated in detail with reference to examples and to a comparative example, without any intention that this should restrict the former.

EXAMPLE 1

A composition which comprised approx. 98% by weight of 2-hydroxyethyl methacrylate (HEMA) and approx. 50 ppm of hydroquinone monomethyl ether was introduced into a short-path evaporator. The pressure in the short-path evaporator and the temperature of the vapours were adjusted such that, according to relation (I), a value of 440 kg/h/m² was obtained. The mass flow density of the vapours, which was established through the evaporation temperature and the condensation temperature, was 27 kg/h/m². Under these conditions, impurities with a low boiling point were removed by evaporation, which left the 2-hydroxyethyl methacrylate to be purified in the residue. No significant polymerization of the composition supplied was found in the short-path evaporator.

The residue obtained from the first evaporation process was introduced into a short-path evaporator for a second time. In this case, the pressure in the short-path evaporator and the temperature of the vapours were established such that, according to relation (I), a value of 112 kg/h/m² was obtained. The mass flow density of the vapours, which was established through the evaporation temperature and the condensation temperature, was 56 kg/h/m². In this evaporation step, 2-hydroxyethyl methacrylate was evaporated. The composition condensed in this step contained approx. 99.5% by weight of 2-hydroxyethyl methacrylate. No significant polymerization of the composition supplied was found in the short-path evaporator.

EXAMPLE 2

A composition which comprised approx. 98% by weight of 2-hydroxyethyl methacrylate (HEMA) and approx. 50 ppm of hydroquinone monomethyl ether was introduced into a short-path evaporator. The pressure in the short-path evaporator and the temperature of the vapours were adjusted such that, according to relation (I), a value of 369 kg/h/m² was obtained. The mass flow density of the vapours, which was established through the evaporation temperature and the condensation temperature, was 32 kg/h/m². Under these conditions, impurities with a low boiling point were removed by evaporation, which left the 2-hydroxyethyl methacrylate to be purified in the residue. No significant polymerization of the composition supplied was found in the short-path evaporator.

The residue obtained from the first evaporation process was introduced into a short-path evaporator for a second time. In this case, the pressure in the short-path evaporator and the temperature of the vapours were established such that, according to relation (I), a value of 296 kg/h/m² was obtained. The mass flow density of the vapours, which was established through the evaporation temperature and the condensation temperature, was 30 kg/h/m². In this evaporation step, 2-hydroxyethyl methacrylate was evaporated. The composition condensed in this step contained approx. 99.5% by weight of 2-hydroxyethyl methacrylate. No significant polymerization of the composition supplied was found in the short-path evaporator.

COMPARATIVE EXAMPLE 1

A composition which comprised approx. 98% by weight of 2-hydroxyethyl methacrylate (HEMA) and approx. 50 ppm of hydroquinone monomethyl ether was introduced into a short-path evaporator. The pressure in the short-path evaporator and the temperature of the vapours were adjusted such that, according to relation (I), a value of 229 kg/h/m² was obtained. The mass flow density of the vapours, which was established through the evaporation temperature and the condensation temperature, was 27 kg/h/m². Under these conditions, impurities with a low boiling point were removed by evaporation, which left the 2-hydroxyethyl methacrylate to be purified in the residue. No significant polymerization of the composition supplied was found in the short-path evaporator.

The residue obtained from the first evaporation process was introduced into a short-path evaporator for a second time. In this case, the pressure in the short-path evaporator and the temperature of the vapours were established such that, according to relation (I), a value of 63 kg/h/m² was obtained. The mass flow density of the vapours, which was established through the evaporation temperature and the condensation temperature, was 81 kg/h/m². In this evaporation step, 2-hydroxyethyl methacrylate was evaporated. The composition condensed in this step contained approx. 98% by weight of 2-hydroxyethyl methacrylate. No significant polymerization of the composition supplied was found in the short-path evaporator.

Comparative example 1 shows clearly that working outside the values specified in relation (I) did not lead to any improvement in the product purity, given that the starting composition already had relatively high purity. It should be considered here that short-path evaporators are customarily not used for fine purification, but for workup of residues.

The invention claimed is:
1. A process for purifying at least one monomer, comprising evaporating at least a portion of the at least one monomer present in a starting composition and then condensing vapors resulting from the evaporation,
wherein
at least a portion of the starting composition is evaporated in a short-path evaporator,
the mass flow density of the vapors, m, is non-zero and selected according to formula (I)

$$\dot{m} \leq 1800 \frac{\text{kg} \cdot \sqrt{K}}{\text{mbar} \cdot \text{m}^2 \cdot h \cdot \sqrt{\frac{\text{kg}}{\text{kmol}}}} \cdot p_i \cdot \left(\frac{\tilde{M}}{T}\right)^{0.5} \quad \text{(I)}$$

wherein
$\tilde{M}$ is the average molar mass of the vapors in the short-path evaporator in kg/kmol,
T is the temperature of the vapors in K,
$p_i$ is the pressure in the short-path evaporator in mbar,
m is the mass flow density of the vapors in kg/(m²·h), said starting composition comprises 1 to 200 ppm of at least one polymerization inhibitor, and
said short-path evaporator has a ratio of evaporator area to condenser area of 0.1 to 10.

2. The process of claim 1, wherein the starting composition comprises at least 95% by weight of the at least one monomer.

3. The process of claim 1, wherein the evaporation is at a temperature in the range from 15° C. to 150° C.

4. The process of claim 1, wherein the starting composition comprises a high-boiling monomer.

5. The process of claim 4, wherein the high-boiling monomer is methacrylic anhydride or a methacrylate.

6. The process of claim 5, wherein the high-boiling monomer is the methacrylate, which is selected from the group consisting of hexyl methacrylate, cyclohexyl methacrylate, 2-ethylhexyl methacrylate, 1,4-butanediol dimethacrylate, glycol dimethacrylate, 2-hydroxyethyl methacrylate, 2-ethoxyethyl methacrylate, decyl methacrylate, tetrahydrofurfuryl methacrylate, octadecyl/stearyl methacrylate, tetraethylene glycol dimethacrylate, 2,2-bis(hydroxymethyl)-1,3-propanediol dimethacrylate, 2-hydroxypropyl methacrylate, 3-hydroxypropyl methacrylate, 1,3-butanediol dimethacrylate, benzyl methacrylate, allyl methacrylate, 2-(2-butoxyethoxy)ethyl methacrylate, trimethylolpropane trimethacrylate, N-3-dimethylaminopropylmethacrylamide, 2-dimethylaminoethyl methacrylate, triethylene glycol dimethacrylate, isobornyl methacrylate, polyethylene glycol methacrylates, isodecyl methacrylate, dodecyl methacrylate, 2-[2-(2-ethoxyethoxy)ethoxy]ethyl methacrylate, 2,3-dihydroxypropyl methacrylate, (2-oxo-1,3-dioxolan-4-yl)methyl methacrylate, 2-carbamoyloxyethyl methacrylate and 1,6-hexanediol dimethacrylate.

7. The process of claim 1, wherein the at least one monomer is acrylic anhydride or an acrylate.

8. The process of claim 7 wherein the at least one monomer is the acrylate, which is at least one selected from the group consisting of hexyl acrylate, cyclohexyl acrylate, 2-ethylhexyl acrylate, 1,4-butanediol diacrylate, glycol diacrylate, 2-hydroxyethyl acrylate, 2-ethoxyethyl acrylate, decyl acrylate, tetrahydrofurfuryl acrylate, octadecyl/stearyl acrylate, tetraethylene glycol diacrylate, 2,2-bis(hydroxymethyl)-1,3-propanediol diacrylate, 2-hydroxypropyl acrylate, 3-hydroxypropyl acrylate, 1,3-butanediol diacrylate, benzyl acrylate, allyl acrylate, 2-(2-butoxyethoxy)ethyl acrylate, trimethylolpropane triacrylate, N-3-dimethylaminopropylmethacrylamide, 2-dimethylaminoethyl acrylate, triethylene glycol diacrylate, isobornyl acrylate, polyethylene glycol acrylates, isodecyl acrylate, dodecyl acrylate, 2-[2-(2-ethoxyethoxy)ethoxy]ethyl acrylate, pentaerythrityl tetraacrylate, pentaerythrityl triacrylate and 1,6-hexanediol diacrylate.

9. The process of claim 1, wherein the residence time of the at least one monomer is in the range from 1 second to 5 minutes.

10. The process of claim 1, wherein at least one component with a low boiling point is withdrawn from the starting composition before the at least one monomer present in the starting composition is evaporated and condensed.

11. The process of claim 10, wherein at least one component with a low boiling point is withdrawn from the starting composition by evaporation in a short-path evaporator.

12. The process of claim 11, wherein the evaporation to remove the at least one component with a low boiling point is at a temperature in the range from 40° C. to 150° C.

13. The process of claim 1, wherein the residue obtained after the evaporation of the at least one monomer is subjected to a residue evaporation and condensation in a short-path evaporator.

14. The process of claim 13, wherein the residue evaporation is at a temperature in the range from 15° C. to 150° C.

15. The process of claim 1, wherein a purified product comprises at least 99% by weight of the at least one monomer.

16. A plant for performing the process of claim 1, wherein the plant comprises at least three short-path evaporators, and
the short-path evaporators are connected to one another such that a residue from a first short-path evaporator is passed into a second short-path evaporator and a residue from the second short-path evaporator is passed into a third short-path evaporator.

17. A plant for performing the process of claim 3, wherein the plant comprises at least three short-path evaporators, and
the short-path evaporators are connected to one another such that a residue from a first short-path evaporator is passed into a second short-path evaporator and a residue from the second short-path evaporator is passed into a third short-path evaporator.

18. A plant for performing the process of claim 11, wherein the plant comprises at least three short-path evaporators, and
the short-path evaporators are connected to one another such that a residue from a first short-path evaporator is passed into a second short-path evaporator and a residue from the second short-path evaporator is passed into a third short-path evaporator.

* * * * *